US012093422B1

(12) United States Patent
Oliveira et al.

(10) Patent No.: US 12,093,422 B1
(45) Date of Patent: Sep. 17, 2024

(54) SYSTEM AND METHOD FOR FACILITATING ACCESS TO DATA SYSTEMS

(71) Applicant: Luma Health, Inc., San Francisco, CA (US)

(72) Inventors: Marcelo Oliveira, San Francisco, CA (US); Aditya Bansod, San Francisco, CA (US)

(73) Assignee: LUMA HEALTH, INC., San Mateo, CA (US)

( * ) Notice: Subject to any disclaimer, the term of this patent is extended or adjusted under 35 U.S.C. 154(b) by 437 days.

(21) Appl. No.: 17/078,970

(22) Filed: Oct. 23, 2020

Related U.S. Application Data

(60) Provisional application No. 62/925,694, filed on Oct. 24, 2019.

(51) Int. Cl.
*G06F 21/62* (2013.01)
*G16H 10/60* (2018.01)

(52) U.S. Cl.
CPC ......... *G06F 21/6245* (2013.01); *G16H 10/60* (2018.01)

(58) Field of Classification Search
CPC .. G06F 21/62; G06F 21/6218; G06F 21/6245; G16H 10/60
See application file for complete search history.

(56) References Cited

U.S. PATENT DOCUMENTS

| | | | |
|---|---|---|---|
| 2005/0209880 A1* | 9/2005 | Drelicharz | G16H 30/20 705/2 |
| 2009/0031005 A1* | 1/2009 | Swanson | H04L 67/142 709/218 |
| 2010/0257612 A1* | 10/2010 | McGuire | G06Q 20/383 726/26 |
| 2012/0179802 A1 | 7/2012 | Narasimhan et al. | |
| 2015/0134733 A1* | 5/2015 | Maturana | H04L 67/12 709/203 |
| 2017/0286698 A1* | 10/2017 | Shetty | H04L 67/10 |

* cited by examiner

*Primary Examiner* — D'Arcy Winston Straub
(74) *Attorney, Agent, or Firm* — Wilson Sonsini Goodrich & Rosati

(57) ABSTRACT

A system and method for facilitating access to data systems are disclosed. In one aspect, the system includes one or more computer systems programmed to perform operations including providing a database access module and providing a local system. The database access module has a core module in communication with a global database having a plurality of records; and a monitor module in communication with the core module and configured to monitor activities of the core module. The local system includes a socket service for establishing persistent socket connections with the core module and the monitor module; a local database in communication with the socket service and including a subset of the plurality of records; and a user application in communication with the socket service and configured to provide a user with access to the subset of the plurality of records.

17 Claims, 6 Drawing Sheets

EHR Access Module

SYSTEM AND METHOD FOR FACILITATING ACCESS TO DATA SYSTEMS

CROSS-REFERENCE TO RELATED APPLICATIONS

This application claims the benefit of U.S. Provisional Patent Application No. 62/925,694, filed Oct. 24, 2019, the entire contents of which are incorporated by reference herein.

TECHNICAL FIELD

The present disclosure relates in general to providing access to databases and, in some examples, to accessing electronic health record database systems by maintaining persistent connections with such systems.

BACKGROUND

Electronic health record (EHR) database systems have become ubiquitous in the healthcare industry for securely storing patient data for healthcare providers. Rather than developing a custom storage solution, healthcare providers continue to rely on EHR database systems to manage their data, allowing the healthcare providers to take advantage of a wide variety of benefits, including, for example: reduced costs, limitation of liabilities under HIPAA, reduction of technical requirements, reduction of system maintenance, reduction of upkeep procedures, access to historical patient data, access to data tools that healthcare providers can use to make decisions about a patient's care, and automatic and streamlined provider workflow. For example, by providing healthcare providers with access to historical patient data, the healthcare providers can be better informed and provide higher quality healthcare analysis and diagnostics, for an improved overall healthcare experience. EHR database systems provide benefits to patients as well, including maintenance of a consistent health record that is accessible and/or transferable across many different healthcare providers or clinics.

Accessing a wide variety of EHR database systems has proven complex and difficult to maintain for private healthcare providers. Due to the large number of different implementations, a healthcare provider must dedicate months of integration engineer time to implement a system that communicates with one or more of these database systems. Further, once the communication platform is in place, the maintenance and resource-heavy implementation can be inefficient and expensive to maintain for each and every database system.

With so many disadvantages, healthcare providers are at the mercy of these EHR database systems; however, the need for healthcare providers to gain access to historical patient data remains essential. There is a need for improved access to a wide variety of EHR database systems.

The foregoing discussion, including the description of motivations for some embodiments of the invention, is intended to assist the reader in understanding the present disclosure, is not admitted to be prior art, and does not in any way limit the scope of any of the claims.

SUMMARY

A system and method for facilitating access to data systems are disclosed. In general, in one aspect, the system includes one or more computer systems programmed to perform operations including providing a database access module. The database access module has a core module in communication with a global database having a plurality of records; and a monitor module in communication with the core module and configured to monitor activities of the core module. The one or more computer systems are further programmed to perform operations including providing a local system. The local system includes a socket service for establishing persistent socket connections with the core module and the monitor module; a local database in communication with the socket service and including a subset of the plurality of records; and a user application in communication with the socket service and configured to provide a user with access to the subset of the plurality of records.

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

It is contemplated that apparatus, systems, methods, and processes of the claimed invention encompass variations and adaptations developed using information from the embodiments described herein. Adaptation and/or modification of the apparatus, systems, methods, and processes described herein may be performed by those of ordinary skill in the relevant art.

It should be understood that the order of steps or order for performing certain actions is immaterial so long as the invention remains operable. Moreover, two or more steps or actions may be conducted simultaneously.

In general, the systems and methods described herein can be used to facilitate access to a variety of EHR database systems. The systems and methods can achieve this, for example, by providing a persistent connection to an EHR access module located within an EHR database system. The persistent connection can enable secure, end-to-end, encrypted communications between a local database system and the EHR database system.

Prior EHR database systems have a wide variety of drawbacks. For example, healthcare providers that use EHR database systems as their primary data storage can lose direct control over their patient's data and are generally limited to functionalities provided by the EHR database provider's system. To access such systems, healthcare providers may be required to purchase and install hardware and software necessary to integrate with an EHR database provider system. Some of these systems, however, may not provide suitable interfaces to their databases. Beyond the adoption costs, the cost of maintenance and upkeep associated with participating in EHR database provider systems can accrue significantly over time, especially when integrating into multiple EHR database systems. Furthermore, backlog or latency issues often occur with large EHR database systems, and this can result in significant amounts of wasted time, both for healthcare providers and patients.

In general, access by healthcare providers to EHR database provider systems can require a widespread understanding of differences among the EHR database provider systems and how to establish and maintain connections with such systems. Furthermore, the current solutions for accessing EHR database provider systems can require resource heavy implementations, such as unnecessary persistent connections and Virtual Private Networks (VPNs). This technical problem results in slower network response and requires more network resources than the present system. Further, developing or building out VPNs for accessing EHR database provider systems can require significant amounts of human effort, expertise, equipment, and/or technical set up.

Figure 1:
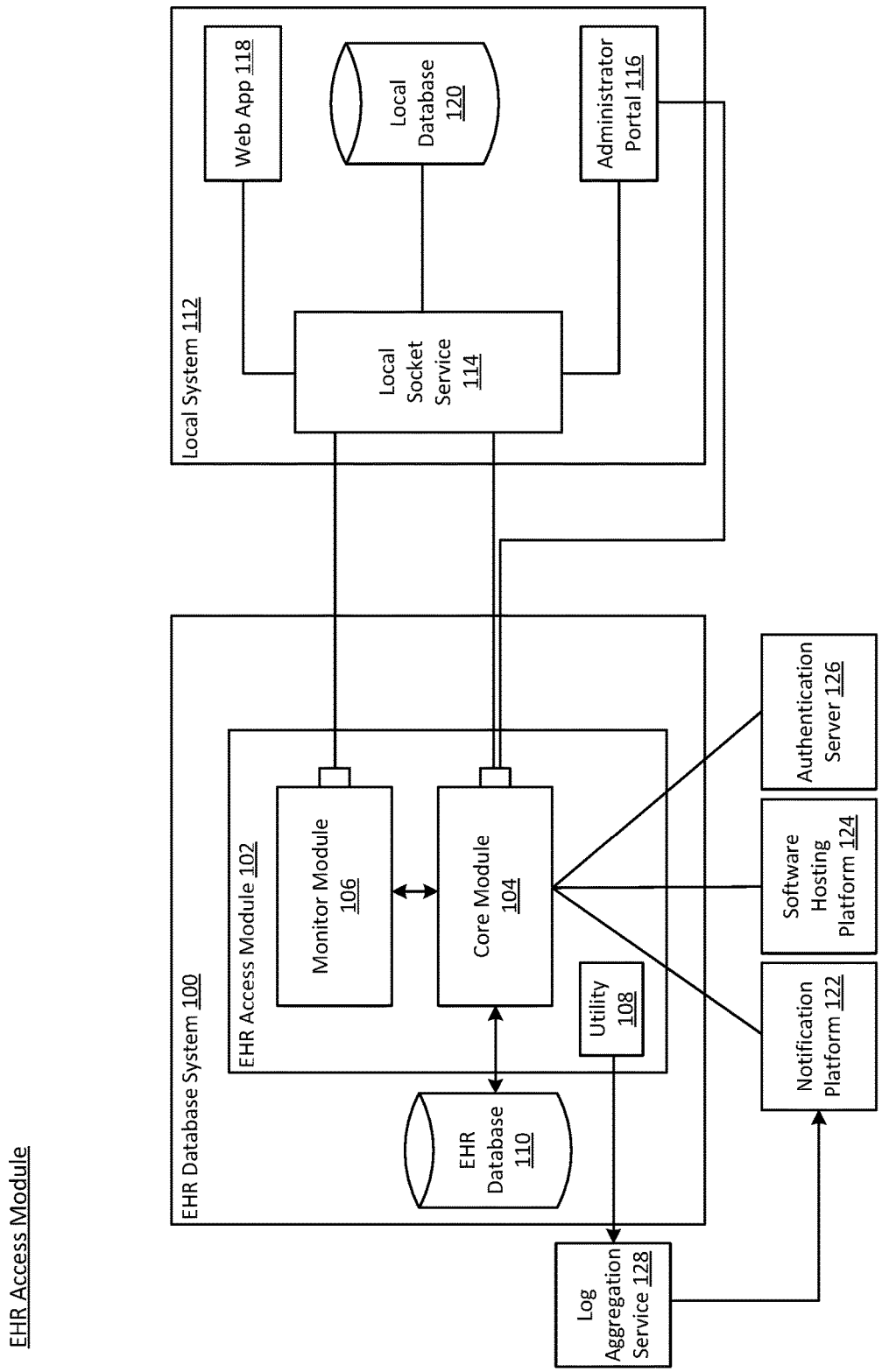
FIG. 1 is a schematic diagram of an EHR database system in communication with a local system, in accordance with certain embodiments.

FIG. 1 illustrates an EHR database system 100 having an EHR access module 102 and an EHR database 110 (alternatively referred to as a "global database") according to some embodiments. The EHR access module 102 can utilize or include a core module 104, a monitor module 106, and/or a utility 108, which can be communicatively coupled to each other. Additionally or alternatively, the core module 104, the monitor module 106, and/or the utility 108 can be communicatively coupled to the EHR database 110. For example, the core module 104 can be communicatively coupled to the EHR database 110 as shown in FIG. 1. The EHR database 110 can include or store health records and other personal data for thousands or millions of patients.

According to some embodiments, the core module 104 and the monitor module 106 can be communicatively coupled to a local system 112 by way of a local socket service 114. The local socket service 114 can communicate with local components of the local system 112 and/or can coordinate sending and receiving external messages to and from such local components, which can include an administrator portal 116, a web app 118, and a local database 120. Additionally or alternatively, local socket service 114 can facilitate communication between the local system 112 and one or more components of the EHR access module 102 (e.g., the core module 104 and/or the monitor module 106). The local socket service 114 may be implemented as a websocket or, more generally, as a tcpsocket. In some embodiments, the administrator portal 116 can be a web-based portal for administrators and/or other users of the local system 112 to directly communicate with and/or control the core module 104. The web app 118 can be or include a client-facing webpage application or client application (e.g., an application installed on a client device) for access by patients, healthcare providers, and/or other users.

The local database 120 can be or include a storage medium containing data used by the local system 112. In some examples, the local database 120 includes a subset of data or records included or stored within the EHR database 110. For example, the local database 120 can store records (e.g., health records and other personal information) related to an operator or user (e.g., a health care provider or health clinic) of the local system 112. By contrast, the EHR database 110 can store many other records in addition to the records related to the operator or user of the local system 112. In preferred examples, the local database 120 and the EHR database 110 can be synced, such that any records shared by the two databases are identical.

According to some embodiments, the core module 104 is communicatively coupled to one or more external services, which may be provided by third parties and/or by an operator of the EHR access module 102 or the local system 112. For example, the core module 104 can be communicatively coupled to external services such as a notification platform 122, a software hosting platform 124, and an authentication server 126, as shown in FIG. 1. In some embodiments, the notification platform 122 may include one or more notification platforms or services, such as the messaging platform SLACK. The notification platform 122 can provide chat rooms, direct messaging, and other messaging services to users of the EHR Access module 102 and/or the local system 112. Additionally or alternatively, the software hosting platform 124 may include one or more software hosting platforms, such as the software hosting platform GITHUB, according to some embodiments. The software hosting platform 124 can provide software updates to the core module 124 or other system components, as needed. The authentication server 126 can be used to authenticate users, files, or other system components.

In some examples, the utility 108 may also be communicatively coupled to one or more external services provided by third parties. For example, the utility 108 can be communicatively coupled to external services such as a log aggregation service 128, as shown in FIG. 1. According to some embodiments, the log aggregation service 128 can communicate with the notification platform 122 to provide notifications regarding log aggregation, as necessary. The log aggregation service 128 may include numerous log aggregation services, such as PAPERTRAIL. In general, the utility 108 can generate or provide logs or log files related to activities or events occurring in the EHR access module 102. Such activities can include, for example, sending, receiving, requesting, updating, or modifying files, data, or records, such as records stored in the EHR database 110.

According to some embodiments, the internal components of the EHR access module 102, including the core module 104 and/or the monitor module 106, may be run as a service within the EHR database system 100 and/or may provide ever-present endpoints for persistent communication to and/or from the local socket service 114. For example, the core module 104 and/or the monitor module 106 may utilize or be stored individually within a JAVA Service Wrapper or other service mechanism that runs applications such as WINDOWS API services or WIN32 services. Additionally or alternatively, the services performed by the components of the EHR access module 102 (e.g., the core module 104 and/or the monitor module 106) may depend on which account(s) is accessing the components. For example, when communicating with the core module 104, the local system 112 may provide an access token, a username, and a password, all of which are specific to a particular user of the local system 112, according to some embodiments. The token can be provisioned at installation (e.g., of the local system 112 or components thereof, such as the web app 118) and stored in the local database 120. After installation, a notification may be sent from the core module 104 to the notification platform 122 to indicate that installation has completed. For example, the notification platform 122 can send a message to inform one or more users of the completed installation.

According to some embodiments, the core module 104 may perform various functions within the EHR database system 100, such as pushing and pulling data to and from the EHR database 110. For example, the core module 104 may receive a request from the local system 112 to retrieve data from the EHR database 110. In response to the request, the core module can retrieve the data from the EHR database 110 and send the data to the local system 112, where it can be accessed by a user of the web app 118 and/or stored in the local database 120. Additionally or alternatively, the core module 104 may be instructed (e.g., by the local system 112) to store new or updated data in the EHR database 110. For example, the core module 104 may receive new or updated data from the local system 112 and store the data in the EHR database 110.

In various implementations, the monitor module 106 may be used to track and monitor the functionality and/or status of the core module 104, for example, as a watchdog service. The monitor module 106 may determine, for example, that certain actions (e.g., accessing, receiving, or sending data or files) being taken by the core module 104 are inappropriate, unauthorized, or risky and, in response, may instruct the core module 104 to stop taking such actions. Additionally or alternatively, the monitor module 106 may clean or remove information accessed or used by the core module 104. For example, the monitor module 106 may implement a software upgrade (e.g., using the software hosting platform 124) for the core module 104. In certain examples, the monitor module 106 may restart certain actions being taken by the core module 104, as described herein.

Figure 2A:
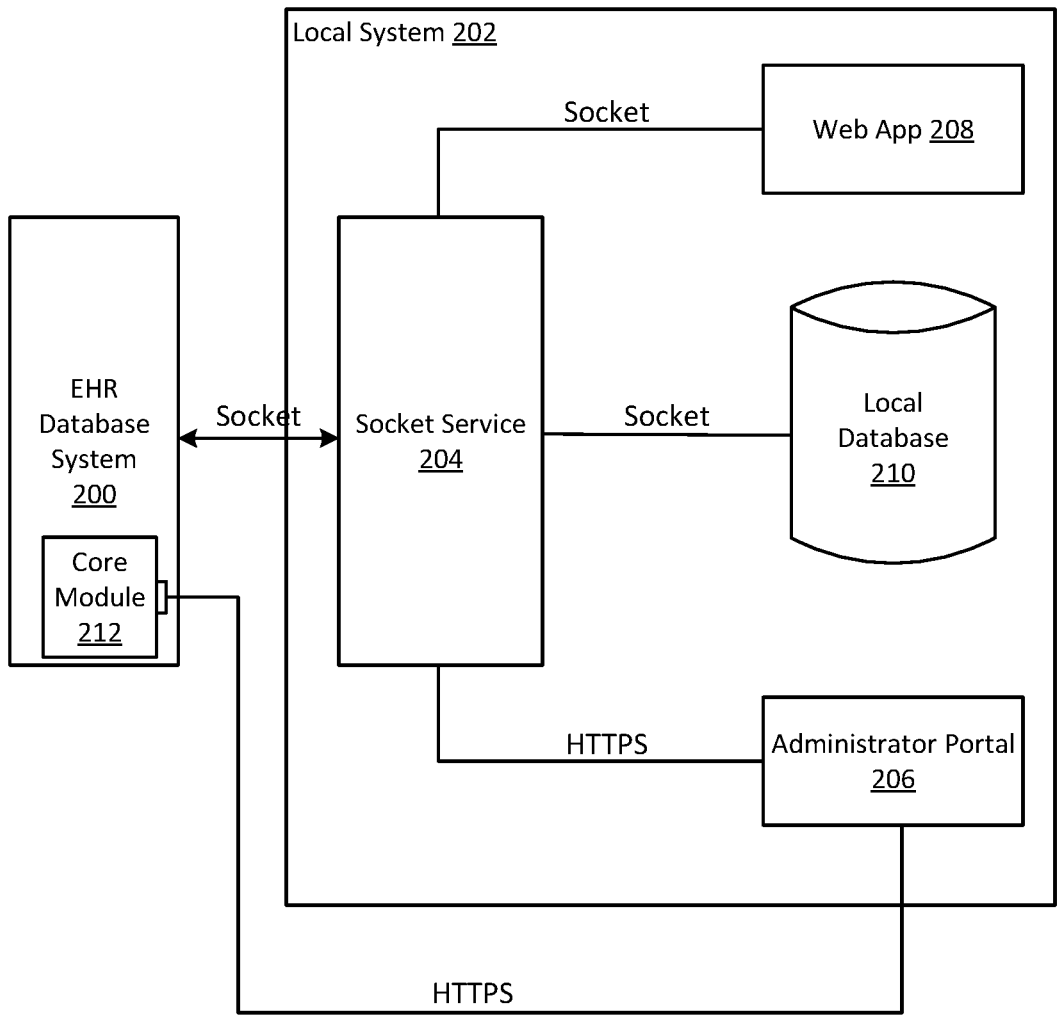
FIG. 2A is a schematic diagram of a system in which a socket service is used to achieve persistent connections between an EHR database system and a local system, in accordance with certain embodiments.

FIG. 2A illustrates an example of a local system 202 (e.g., the local system 112) for accessing information stored in or otherwise interacting with an EHR database system 200 (e.g., the EHR database system 100), according to some embodiments. The EHR database system 200 may communicate with the local system 202 by way of a socket service 204. The local system 202 can include the socket service 204, an administrator portal 206, a web app 208, and a local database 210, which may be the same as the local socket service 114, the administrator portal 116, the web app 118, and the local database 120, respectively. In various examples, the local system 202 can be used or operated by a healthcare provider, such as a doctor's office or a health clinic. A user of the local system 202 can be, for example, a doctor, a nurse, a nurse practitioner, or other healthcare professional.

The socket service 204 can be communicatively coupled to the administrator portal 206, the web app 208, and the local database 210. According to some embodiments, the socket service 204 securely communicates with the administrator portal 206 using secure encrypted internet protocols, such as Hypertext Transfer Protocol Secure (HTTPS). The administrator portal 206 can communicate with the EHR database system 200 by way of socket service 204. Additionally or alternatively, the administrator portal 206 may communicate directly with components of the EHR database system 200, such as the core module 212, without using the socket service 204. Such direct communications can facilitate the sending of commands from the administrator portal 206 to the core module 212.

According to some embodiments, the socket service 204 can maintain a persistent socket connection to the web app 208 to facilitate communication therebetween. The web app 208 can communicate with the EHR database system 200 by way of the socket service 204. The web app 208 can provide a web-based, client-facing interface to provide clients of local system 202 access to data and functionalities provided by the EHR database system 200. Persistent socket connections between the web app 208, the socket service 204, and the EHR database system 200 can provide an efficient communication pipeline.

According to some embodiments, the socket service 204 maintains a persistent socket connection to the local database 210 to facilitate communication therebetween. The local database 210 can provide data as requested by the socket service 204 or other components of the local system 202. The data stored within local database 210 may be updated periodically or on-demand. The persistent socket connections with local database 210 can provide an efficient communication pipeline.

In various examples, the socket service 204 can maintain persistent socket connections to various components of the EHR database system 200 and the local system 202. For example, the socket service 204 can maintain persistent socket connections between the web app 208 and the core module 212. Additionally or alternatively, persistent socket connections can be provided to one or more databases, such as the local database 210 and any databases in the EHR database system 200 (e.g., the EHR database 110).

Figure 2B:
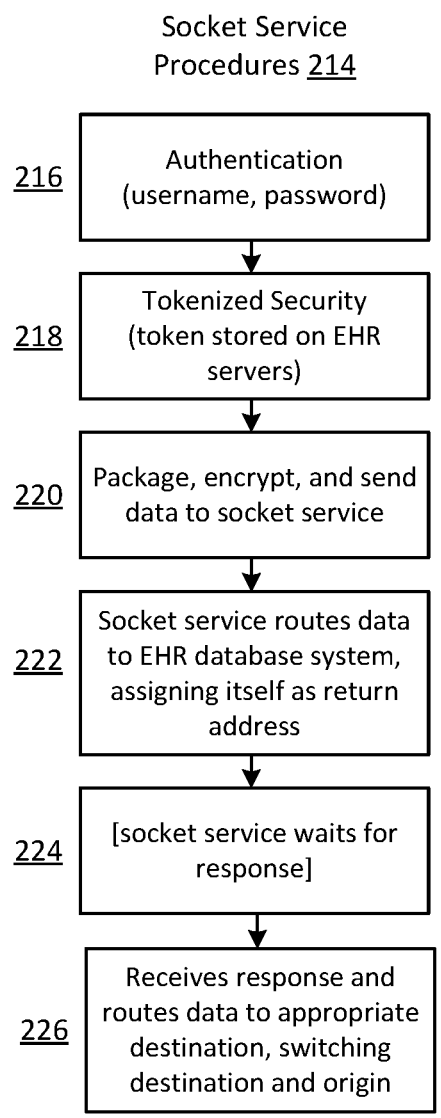
FIG. 2B is a flowchart of a method of using a socket service to facilitate communications with an EHR database system, in accordance with certain embodiments.

Referring to FIG. 2B, according to some embodiments, the socket service 204 can include or utilize a socket service process 214 to facilitate communication using persistent socket connections. The socket service process 214 can authenticate a user by providing a username and password at step 216. The socket service process 214 can further include or utilize tokenized security, as follows: a security token is provided at step 218; data is packaged, encrypted (e.g., using Transport Security Layer (TLS) or HTTPS/TLS encryption) and sent at step 220; the data is routed to the EHR database system and the socket service 204 is assigned as a return address at step 222; the socket service 204 waits for a response at step 224; and finally, at step 226, a response is received and data is routed to an appropriate destination according to a header of the received response. Additionally or alternatively, in some examples, a communication protocol for the socket service 204 may require a communication or communication content to be cryptographically signed, for example, to confirm or validate an identity of a sender of the communication.

The persistent socket connections utilized by the systems and methods described herein provide many advantages over other Internet protocols. For example, maintaining persistent socket connections between components of the system can significantly reduce network congestion and CPU usage by avoiding handshaking or other inefficiencies associated with establishing new connections. Advantageously, the persistent connections can reduce latency in subsequent requests (e.g., due to no handshaking), reduce CPU usage and round-trips (e.g., due to fewer new connections and handshakes), reduce network congestion (e.g., due to fewer TCP connections), and/or enable HTTP pipelining of responses and requests.

In various examples, the systems and methods described herein can utilize File Transfer Protocol (FTP) or Hypertext Transfer Protocol (HTTP) connections. For example, referring again to FIG. 1, a connection between the core module 104 and the EHR database 110 can utilize FTP (or FTP secured with SSL/TLS (FTPS) or SSH File Transfer Protocol (SFTP)), while one or more other connections (e.g., between the core module 104 and the local socket service 114) can utilize HTTP (or HTTP persistent connection).

Figure 3:
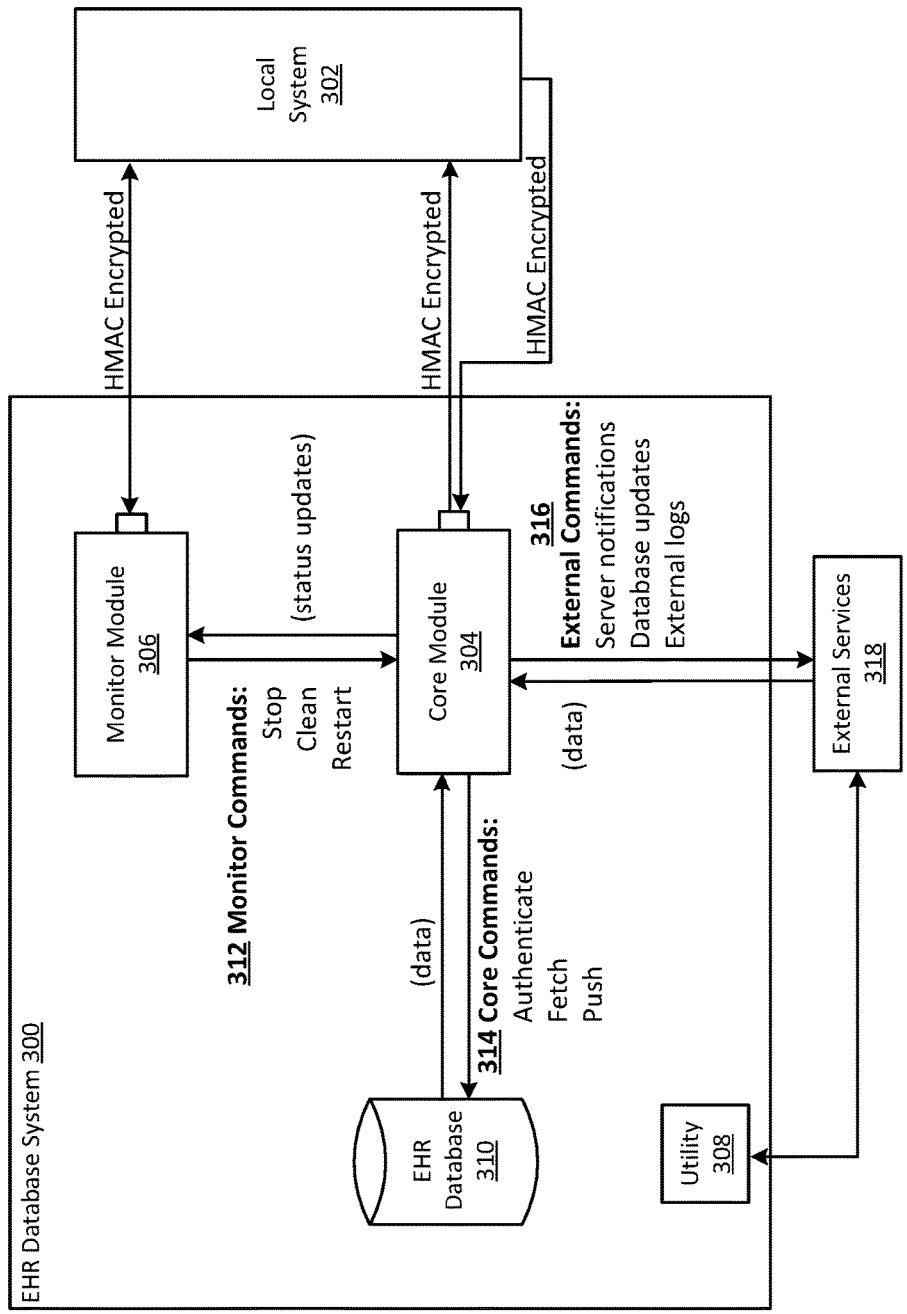
FIG. 3 is a schematic diagram of communications occurring between components of an EHR database system, in accordance with certain embodiments.

FIG. 3 illustrates internal operations of an EHR database system 300 (e.g., the EHR database system 100), according to some embodiments. The EHR database system 300 may communicate with a local system 302 (e.g., the local system 112). The EHR database system 300 includes a core module 304, a monitor module 306, a utility 308, and an EHR database 310 (e.g., which may be the same as the core module 104, the monitor module 106, the utility 108, and the EHR database 110, respectively).

In the depicted example, the monitor module 306 is communicatively coupled to the core module 304 (e.g., using a persistent socket connection) and may transmit monitor commands 312 to the core module 304 to perform monitoring procedures, according to some embodiments. Monitor commands 312 may include, for example, among others, a stop command, a clean command, and/or a restart command, as described herein. Such commands can be triggered, for example, when the monitor module 306 fails to detect a successful connection between the core module 304 and another system component. The monitor commands 312 can be issued in an effort to self-heal or repair the connection. The core module 304 may transmit data to monitor module 306, in response to one of the monitor commands 312 or independently without prompt. According to some embodiments, the data transmitted from the core module 304 to the monitor module 306 may include, but is not limited to, status updates, activity logs, error messages, or other information related to the core module 304 or associated activities.

In various examples, the core module 304 and the monitor module 306 may transmit and receive securely authenticated messages to and from the local system 302. For example, the core module 304 and the monitor module 306 may transmit hash-based message authentication code (HMAC) messages or other message authentication code (MAC) messages, which may be cryptographically authenticated by the receiving system (e.g., the local system 302) using a digital key. In general, any messages sent between the local system 302 and the core module 304 or the monitor module 306 can utilize cryptographic authentication (e.g., HMAC), for example, so that an identify of the sender can be validated.

In certain implementations, the core module 304 is communicatively coupled to the EHR database 310 (e.g., using a persistent socket connection) and may transmit core commands 314 to the EHR database 310, according to some embodiments. The core commands 314 may include, for example, among others, authenticate, fetch, and push. The authenticate command may be used to authenticate a user, a file, or other system component. The fetch and push commands may be used to retrieve and store data in the EHR database 310, respectively. Additionally or alternatively, the core commands 314 may include requests for access limitations to the EHR database 310 and/or whitelists of users or modules that provide security shortcuts thereto. In response, the EHR database 310 may return data to the core module 304, for example, depending on the core command 314 transmitted. The data returned to core module 304 may include, but is not limited to, confirmation messages, error messages, queries, updates to the EHR database 310, data stored within the EHR database 310, or other information related to the EHR database 310.

Core module 304 can be further communicatively coupled to external services 318, which may include, for example, the notification platform 122, the software hosting platform 124, the authentication server 126, and/or the log aggregation service 128. The core module 304 may transmit external commands 316 to the external services 318 to perform various external procedures, according to some embodiments. For example, the external commands 316 may include, among others, push server notifications, request for driver updates, and save external logs. In some examples, the external commands 316 may include data relevant to the commands being transmitted, some of which may include, for example, a notification message, a request to fetch data from a server, or data containing logs to store externally. In response, one or more of the external services 318 may return data to the core module 304, depending on the external command 316 transmitted. According to some embodiments, the data returned by the external services 318 to the core module 304 may include, but is not limited to, confirmation messages, error messages, install packages to be run on the core module 304, or other information related to the external services 318 or the core module 304.

According to some embodiments, the utility 308 may handle a subset of external commands 316 that may be transmitted to external services 318, for example, for the purpose of storing data externally and/or performing external procedures. For example, the utility 308 may transmit data logs to the external services 318, which may aggregate or compile the data logs for review or analysis (e.g., by users or operators of the EHR database system 300 or the local system 302). Data may or may not be returned from the external services 318 to utility 308, depending on the external commands issued by the utility 308.

Figure 4:
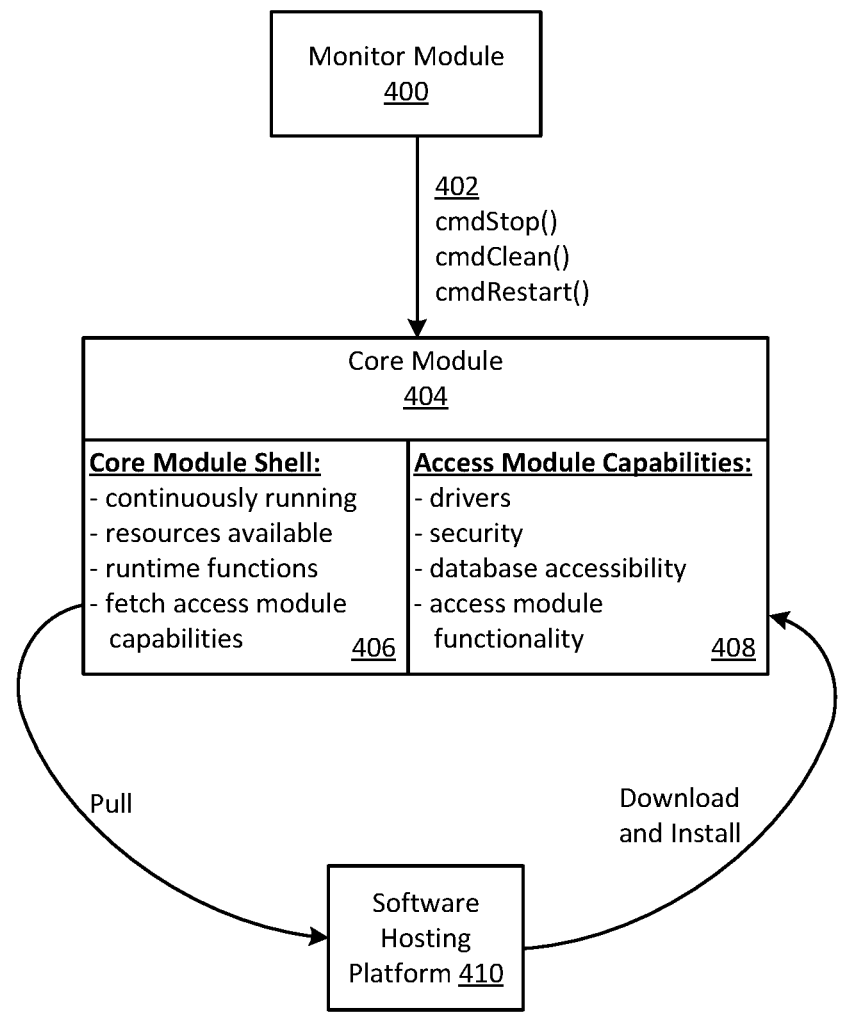
FIG. 4 is a schematic diagram of a core module for an EHR database system, in accordance with certain embodiments.

FIG. 4 illustrates various operations that can be performed by a monitor module 400 (e.g., the monitor module 106) and a core module 404 (e.g., the core module 104), according to an exemplary embodiment. The core module 404 can include a core module shell 406 and access module capabilities 408. The core module shell 406 can include or utilize a minimum functionality of the core module 404, including a request to fetch new access module capabilities 408. Access module capabilities 408 can include or provide capabilities that support the main functionality of the EHR access module (e.g., the EHR access module 102), including additional drivers, security protocols, EHR database capabilities, and/or other access module functionalities.

As a demonstrative example, the monitor module 400 may transmit a list of commands 402 to core module 404, which can include, for example, stop, clean, and/or restart commands, as described herein. In response, the core module 404 can execute the stop command, which can end all processes within the access module capabilities 408. The core module 404 can then execute the clean command, which can delete an entirety of access module capabilities 408 and/or related data. The core module 404 can then execute the restart command, which can reboot the core module 404. The reboot process of the core module 404 can begin by checking whether or not the access module capabilities 408 are up-to-date. The core module shell 406 can determine, for example, that the access module capabilities 408 need updating and, in response, can fetch and/or install updates from a software hosting platform 410 (e.g., the software hosting platform 124). The restart process can be completed once the access module capabilities 408 have been updated or installed, according to some embodiments.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept.

In some examples, some or all of the processing described above can be carried out on a personal computing device, on one or more centralized computing devices, or via cloud-based processing by one or more servers. Some types of processing can occur on one device and other types of processing can occur on another device. Some or all of the data described above can be stored on a personal computing device, in data storage hosted on one or more centralized computing devices, and/or via cloud-based storage. Some data can be stored in one location and other data can be stored in another location. In some examples, quantum computing can be used and/or functional programming languages can be used. Electrical memory, such as flash-based memory, can be used.

Figure 5:
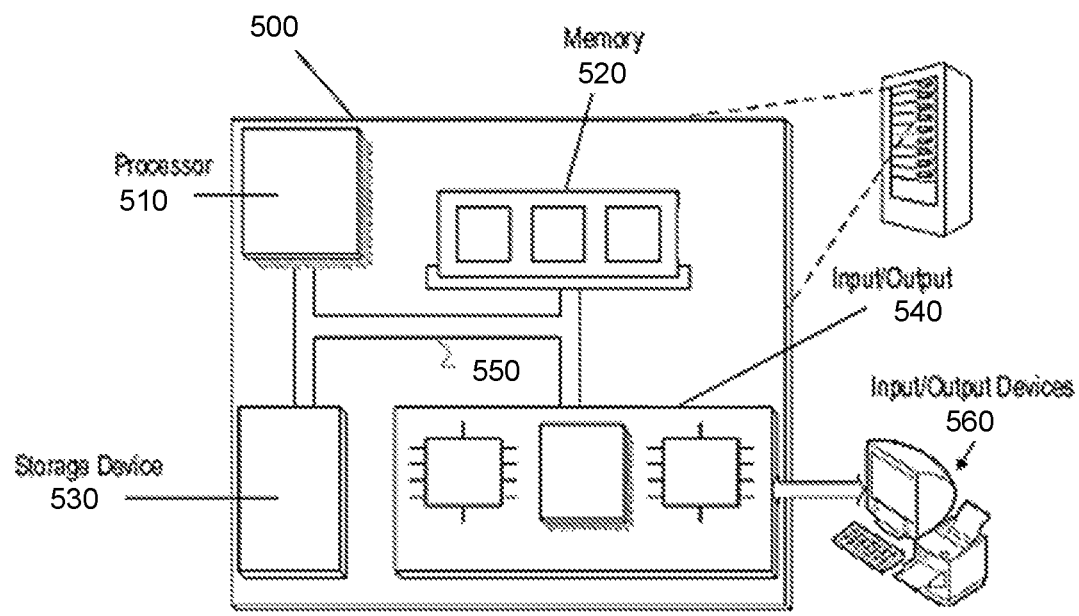
FIG. 5 is a block diagram of an example computer system, in accordance with certain embodiments.

FIG. 5 is a block diagram of an example computer system 500 that may be used in implementing the technology described herein. General-purpose computers, network appliances, mobile devices, or other electronic systems may also include at least portions of the system 500. The system 500 includes a processor 510, a memory 520, a storage device 530, and an input/output device 540. Each of the components 510, 520, 530, and 540 may be interconnected, for example, using a system bus 550. The processor 510 is capable of processing instructions for execution within the system 500. In some implementations, the processor 510 is a single-threaded processor. In some implementations, the processor 510 is a multi-threaded processor. The processor 510 is capable of processing instructions stored in the memory 520 or on the storage device 530.

The memory 520 stores information within the system 500. In some implementations, the memory 520 is a non-transitory computer-readable medium. In some implementations, the memory 520 is a volatile memory unit. In some implementations, the memory 520 is a non-volatile memory unit.

The storage device 530 is capable of providing mass storage for the system 500. In some implementations, the storage device 530 is a non-transitory computer-readable medium. In various different implementations, the storage device 530 may include, for example, a hard disk device, an optical disk device, a solid-state drive, a flash drive, or some other large capacity storage device. For example, the storage device may store long-term data (e.g., database data, file system data, etc.). The input/output device 540 provides input/output operations for the system 500. In some implementations, the input/output device 540 may include one or more network interface devices, e.g., an Ethernet card, a serial communication device, e.g., an RS-232 port, and/or a wireless interface device, e.g., an 802.11 card, a 3G wireless modem, or a 4G wireless modem. In some implementations, the input/output device may include driver devices configured to receive input data and send output data to other input/output devices, e.g., keyboard, printer and display devices 560. In some examples, mobile computing devices, mobile communication devices, and other devices may be used.

In some implementations, at least a portion of the approaches described above may be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 530 may be implemented in a distributed way over a network, such as a server farm or a set of widely distributed servers, or may be implemented in a single computing device.

Although an example processing system has been described in FIG. 5, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "system" may encompass all kinds of apparatus, devices, and machines for processing data, including by way of example a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

Terminology

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Each numerical value presented herein, for example, in a table, a chart, or a graph, is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A system for accessing a database, the system comprising:
   a non-transitory computer-readable medium having instructions stored thereon that, when executed by one or more computer processors, cause the one or more computer processors to perform a method, the method comprising:
      providing a database access module comprising:
         a core module comprising circuitry and in communication with a global database comprising a plurality of records, wherein the core module is configured to retrieve data from the global database to be provided to a local system; and
         a monitor module comprising circuitry, in communication with the core module, and configured to monitor activities of the core module; and
      providing the local system comprising:
         a socket service for establishing persistent socket connections with the core module and the monitor module;
         a local database in communication with the socket service and comprising a subset of the plurality of records; and
         a user application in communication with the socket service and configured to provide a user with access to the subset of the plurality of records.

2. The system of claim 1, wherein the plurality of records comprises electronic health records.

3. The system of claim 1, wherein the core module is configured to provide the retrieved data to the local system through the socket service.

4. The system of claim 1, wherein the core module is configured to receive data from the local system through the socket service and push the received data to the global database.

5. The system of claim 1, wherein the monitor module is configured to control the activities of the core module.

6. The system of claim 1, wherein the monitor module is configured to issue stop, clean, and restart commands to the core module.

7. The system of claim 1, wherein the database access module further comprises a utility comprising circuitry configured to transmit logs from the database access module to a log aggregation service.

8. The system of claim 1, wherein the core module is in communication with at least one of a notification platform, a software hosting platform, or an authentication server.

9. A computer-implemented method of accessing a database, the method comprising:
 providing a database access module comprising:
  a core module in communication with a global database comprising a plurality of records, wherein the core module is configured to retrieve data from the global database to be provided to a local system; and
  a monitor module in communication with the core module and configured to monitor activities of the core module; and
 providing the local system comprising:
  a socket service for establishing persistent socket connections with the core module and the monitor module;
  a local database in communication with the socket service and comprising a subset of the plurality of records; and
  a user application in communication with the socket service and configured to provide a user with access to the subset of the plurality of records.

10. The method of claim 9, wherein the plurality of records comprises electronic health records.

11. The method of claim 9, wherein the core module is configured to provide the retrieved data to the local system through the socket service.

12. The method of claim 9, wherein the core module is configured to receive data from the local system through the socket service and push the received data to the global database.

13. The method of claim 9, wherein the monitor module is configured to control the activities of the core module.

14. The method of claim 9, wherein the monitor module is configured to issue stop, clean, and restart commands to the core module.

15. The method of claim 9, wherein the database access module further comprises a utility configured to transmit logs from the database access module to a log aggregation service.

16. The method of claim 9, wherein the core module is in communication with at least one of a notification platform, a software hosting platform, or an authentication server.

17. A non-transitory computer-readable medium having instructions stored thereon that, when executed by one or more computer processors, cause the one or more computer processors to perform operations comprising:
 providing a database access module comprising:
  a core module comprising circuitry and in communication with a global database comprising a plurality of records, wherein the core module is configured to retrieve data from the global database to be provided to a local system; and
  a monitor module comprising circuitry, in communication with the core module, and configured to monitor activities of the core module; and
 providing the local system comprising:
  a socket service for establishing persistent socket connections with the core module and the monitor module;
  a local database in communication with the socket service and comprising a subset of the plurality of records; and
  a user application in communication with the socket service and configured to provide a user with access to the subset of the plurality of records.

* * * * *